(12) United States Patent
Stockman et al.

(10) Patent No.: US 7,569,188 B2
(45) Date of Patent: Aug. 4, 2009

(54) SURFACE PLASMON AMPLIFICATION BY STIMULATED EMISSION OF RADIATION (SPASER)

(75) Inventors: Mark I. Stockman, Atlanta, GA (US); David J. Bergman, Ramat Hasharon (IL)

(73) Assignees: Ramot At Tel-Aviv University Ltd, Tel-Aviv (IL); The Georgia State University Research Foundation, Atlanta, GA (US)

(*) Notice: Subject to any disclaimer, the term of this patent is extended or adjusted under 35 U.S.C. 154(b) by 831 days.

(21) Appl. No.: 10/751,368

(22) Filed: Jan. 5, 2004

(65) Prior Publication Data

US 2004/0155184 A1  Aug. 12, 2004

Related U.S. Application Data

(60) Provisional application No. 60/437,760, filed on Jan. 3, 2003.

(51) Int. Cl.
*G01N 21/00* (2006.01)
(52) U.S. Cl. .............. 422/82.05; 422/82.06; 422/82.07; 422/82.08; 422/82.09
(58) Field of Classification Search ............ None
See application file for complete search history.

(56) References Cited

OTHER PUBLICATIONS

Kulakovich et al. "Enhanced Luminescence of CdSe Quantum Dots on Gold Colloids", NanoLetters, 2002, v. 2, No. 12, pp. 1449-1452, published on Web Nov. 7, 2002.*
Shimizu et al. "Surface-Enhanced Emission from Single Semiconductor Nanocrystals", Phys. Rev. Lett, Sep. 2002, v. 89, No. 11., pp. 117401-1—117401-4.*
Gryczynski et al. "Surface-plasmon Coupled Emission of Quantum Dots", J. Phys. Chem. B, 2005, v. 109, pp. 1088-1093.*
Stockman et al.; *Localization versus Delocalization of Surface Plasmons in Nanosystems: Can One State Have Both Characteristics?*; Physical Review Letters; vol. 87, No. 16; (Oct. 15, 2001); pp. 167401-1-167401-4.

* cited by examiner

*Primary Examiner*—Yelena G Gakh
(74) *Attorney, Agent, or Firm*—King & Spalding LLP

(57) ABSTRACT

A nanostructure is used to generate a highly localized nanoscale optical field. The field is excited using surface plasmon amplification by stimulated emission of radiation (SPASER). The SPASER radiation consists of surface plasmons that undergo stimulated emission, but in contrast to photons can be localized within a nanoscale region. A SPASER can incorporate an active medium formed by two-level emitters, excited by an energy source, such as an optical, electrical, or chemical energy source. The active medium may be quantum dots, which transfer excitation energy by radiationless transitions to a resonant nanosystem that can play the same role as a laser cavity in a conventional laser. The transitions are stimulated by the surface plasmons in the nanostructure, causing the buildup of a macroscopic number of surface plasmons in a single mode.

33 Claims, 13 Drawing Sheets

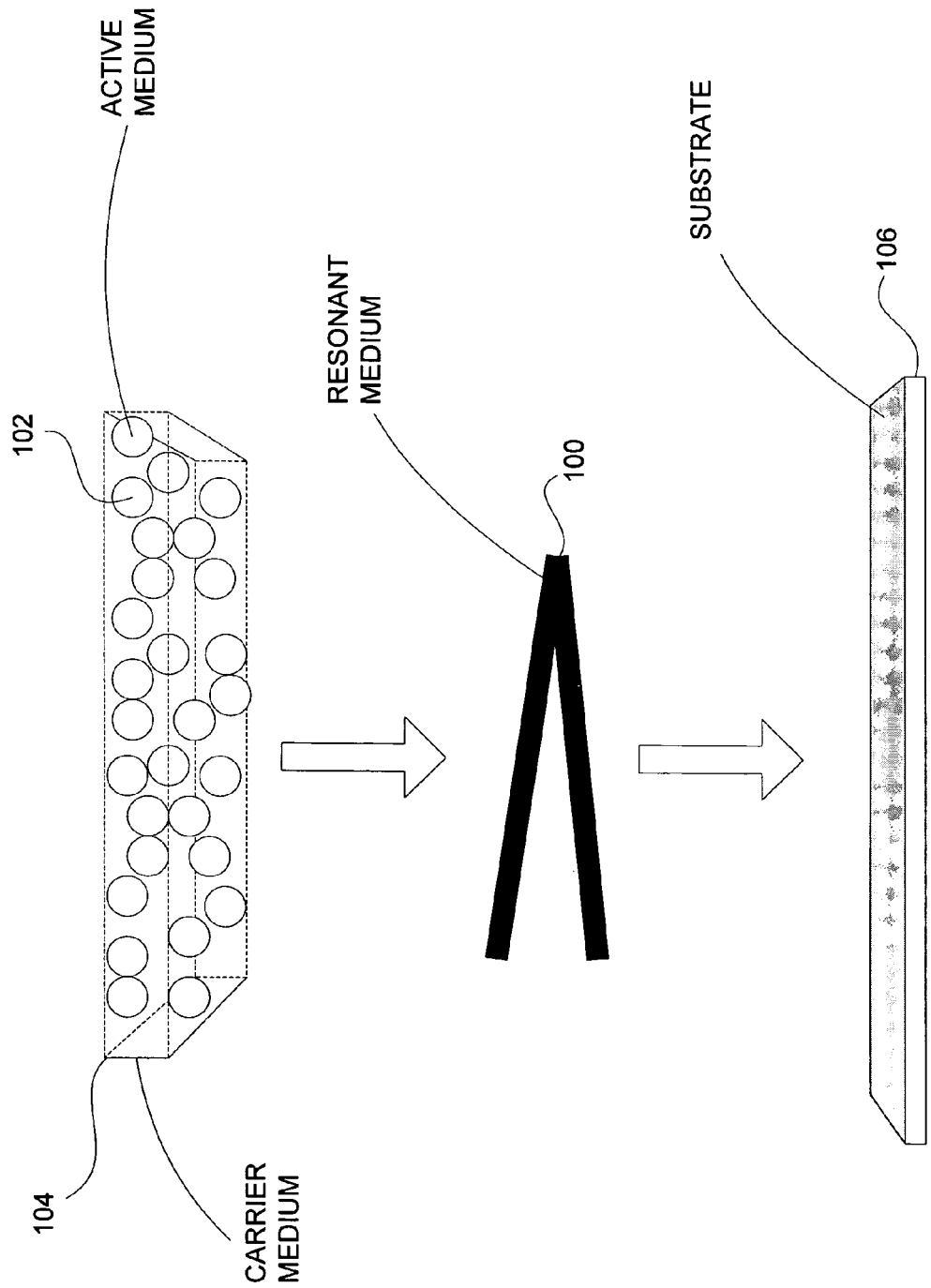

FIG. 12a
$\hbar\omega_n = 1.15\,\text{eV}$
$\alpha_n = 12,\ f_n = 5\times 10^{-3}$
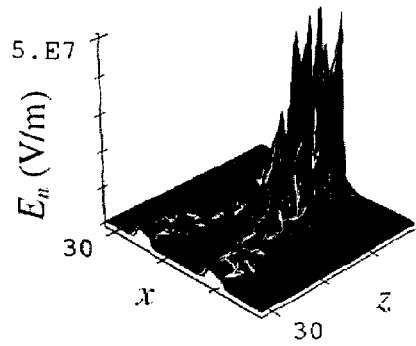
FIG. 12b
$\hbar\omega_n = 1.18\,\text{eV}$
$\alpha_n = 11,\ f_n = 3\times 10^{-12}$
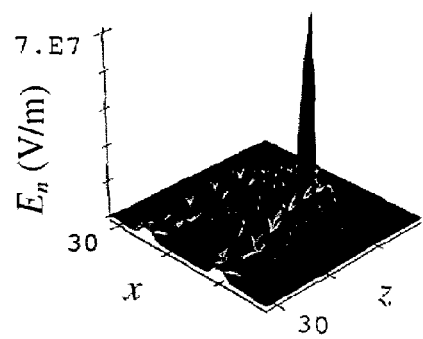
$\hbar\omega_n = 1.63\,\text{eV}$
$\alpha_n = 5.7,\ f_n = 7\times 10^{-14}$
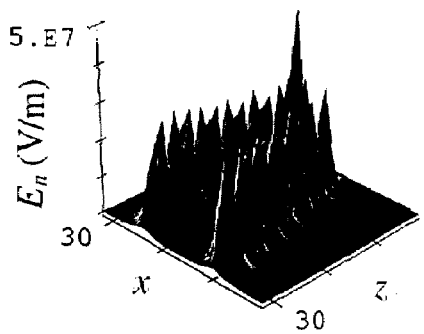
FIG. 12c
$\hbar\omega_n = 1.56\,\text{eV}$
$\alpha_n = 5.3,\ f_n = 1\times 10^{-3}$
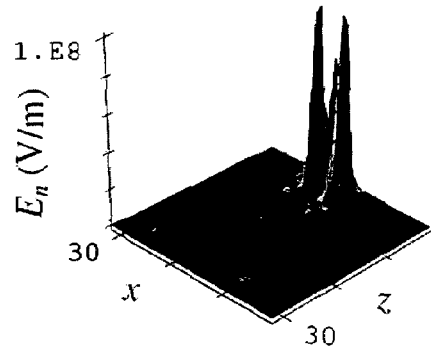
FIG. 12d

SURFACE PLASMON AMPLIFICATION BY STIMULATED EMISSION OF RADIATION (SPASER)

STATEMENT REGARDING RELATED APPLICATIONS

This application claims the benefit of priority to U.S. Provisional Application No. 60/437,760, entitled, "Surface Plasmon Amplification By Stimulated Emission of Radiation," filed Jan. 3, 2003, the contents of which are hereby incorporated by reference.

STATEMENT OF GOVERNMENT RIGHTS

This invention was made with government support under Grant No. DE-FG02-01ER15213 awarded by the U.S. Department of Energy. The government may have certain rights in the invention.

FIELD OF THE INVENTION

The present invention relates to generating surface plasmons and more specifically relates to quantum generation of localized optical fields on a nanoscale.

BACKGROUND OF THE INVENTION

Electromagnetic radiation propagates as a wave and, in an isotropic uniform medium, consists of oscillating electric and magnetic fields at right angles to one another and to the propagation direction. Electromagnetic radiation comes in discrete packets known as photons. Photons are the basic unit of light. Photons were first postulated by Planck who showed that electromagnetic radiation had to come in discrete units. Because the energy of photons is directly proportional to their frequency, low-energy photons have low frequencies, while high-energy photons have high frequencies. Low-energy photons include radio waves or microwaves, medium-energy photons include visible light, high-energy photons include X-rays, while those having higher energy still are called gamma rays.

LASER is an acronym for "light amplification by stimulated emission of radiation." The first working laser was built in 1960 and made use of optical pumping of a ruby crystal from a flash lamp. The first continuous laser was produced in 1962 using an arc lamp instead of a flash lamp. Since its development, the laser has been used in a multitude of different applications and has become virtually ubiquitous in consumer electronics. A laser emits an electromagnetic wave having electrical field and magnetic field components. Unfortunately, the light emitted by a laser is an electromagnetic wave that cannot be localized at target regions significantly smaller than the wavelength (on order of fractions of a micron for visible light). So, while lasers are an extraordinarily valuable technology, the use of lasers is generally limited to applications in which the target regions are significantly larger than the wavelength of the laser light. This has excluded the practical use of the laser from various biotechnical applications, for example, where the target region is on the order of a few nanometers (1 nanometer (nm)=$10^{-9}$ meter) and is thus 100 to 1000 times smaller than a typical laser wavelength.

There are several well-known devices and methods for channeling the energy of laser light to the nanoscale using surface plasmon resonances. One of them is apertureless NSOM (near-field scanning optical microscope), which uses a sharp metal (usually, gold or silver) tip with the radius of curvature of typically 30 to 50 nm, irradiated by an external laser light. This radiation excites surface plasmon oscillations at the tip, creating high oscillating local fields localized at the tip in nanoscale areas with sizes comparable to tip's curvature. These localized oscillating electric fields are used to probe surfaces and molecules with resolutions on the order of approximately 30-100 nm. The limitation of such devices is that the only a negligible (typically, $10^{-7}$) fraction of the laser energy is concentrated on nanoscale. It is, therefore, difficult or impossible to control properties (e.g., specific plasmon modes excited, shape of the localization region, and polarization and amplitude of the fields). It also is difficult to fabricate an effective nanometer tip—conventionally, only one in 20 tips work satisfactorily.

Another group of devices and methods have been developed to exploit surface plasmons for the sensing of chemical and biological agents. Such a device normally includes an interface between a metal and dielectric medium that possesses surface plasmon modes. These modes are excited by an external laser source to create oscillating electric fields at this interface. These fields excite molecules adsorbed at this interface, where the detection is done by either measuring absorption resonances of the excitation laser light, or by detecting Raman scattering from those adsorbates. The limitation of such methods and devices is that they generally are only usable with a comparatively large number of molecules, are incapable of detection single molecules or biological particles, and they do not have nanometer-scale spatial resolution in the lateral direction.

Therefore, there is a need in the art for the generation of an oscillating electric field on a nanoscale (i.e., on the order of 1-100 nanometers). This electric field should result from the emission of surface plasmons (electric oscillations in matter) and should be able to be localized on a target region on the order of nanometers, i.e., by a factor of thousand shorter than the practical target region for a laser.

SUMMARY OF THE INVENTION

A nanostructure is used to generate a highly localized nanoscale optical field. The field is excited using surface plasmon amplification by stimulated emission of radiation (SPASER). The SPASER radiation consists of surface plasmons that undergo stimulated emission, but in contrast to photons can be localized within a nanoscale region. A SPASER can incorporate an active medium formed by two-level emitters, excited by an energy source, such as an optical, electrical, or chemical energy source. The active medium may be quantum dots, which transfer excitation energy by radiationless transitions to a resonant nanosystem that can play the same role as a laser cavity in a conventional laser. The transitions are stimulated by the surface plasmons in the nanostructure, causing the buildup of a macroscopic number of surface plasmons in a single mode. The SPASER may not emit light waves, because its two-level emitters undergo radiationless transitions where their excitation energy is transformed into the quasi-static electric field energy of surface plasmons of the nanostructure. There are a multitude of possible applications of the SPASER in nanoscience and nanotechnology, including for near-field, in particular nonlinear, optical probing and nanomodification.

The various aspects of the present invention may be more clearly understood and appreciated from a review of the following detailed description of the disclosed embodiments and by reference to the drawings and claims.

BRIEF DESCRIPTION OF THE DRAWINGS

FIG. 1a is a block diagram illustrating the primary components of an exemplary embodiment of the present invention.

FIGS. 12a, 12b, 12c, and 12d are plots showing RMS amplitude in a metal nano-structure for eigenmodes with the highest SPASER gains at two spatial maxima.

DETAILED DESCRIPTION OF THE EXEMPLARY EMBODIMENTS

Figure 1B:
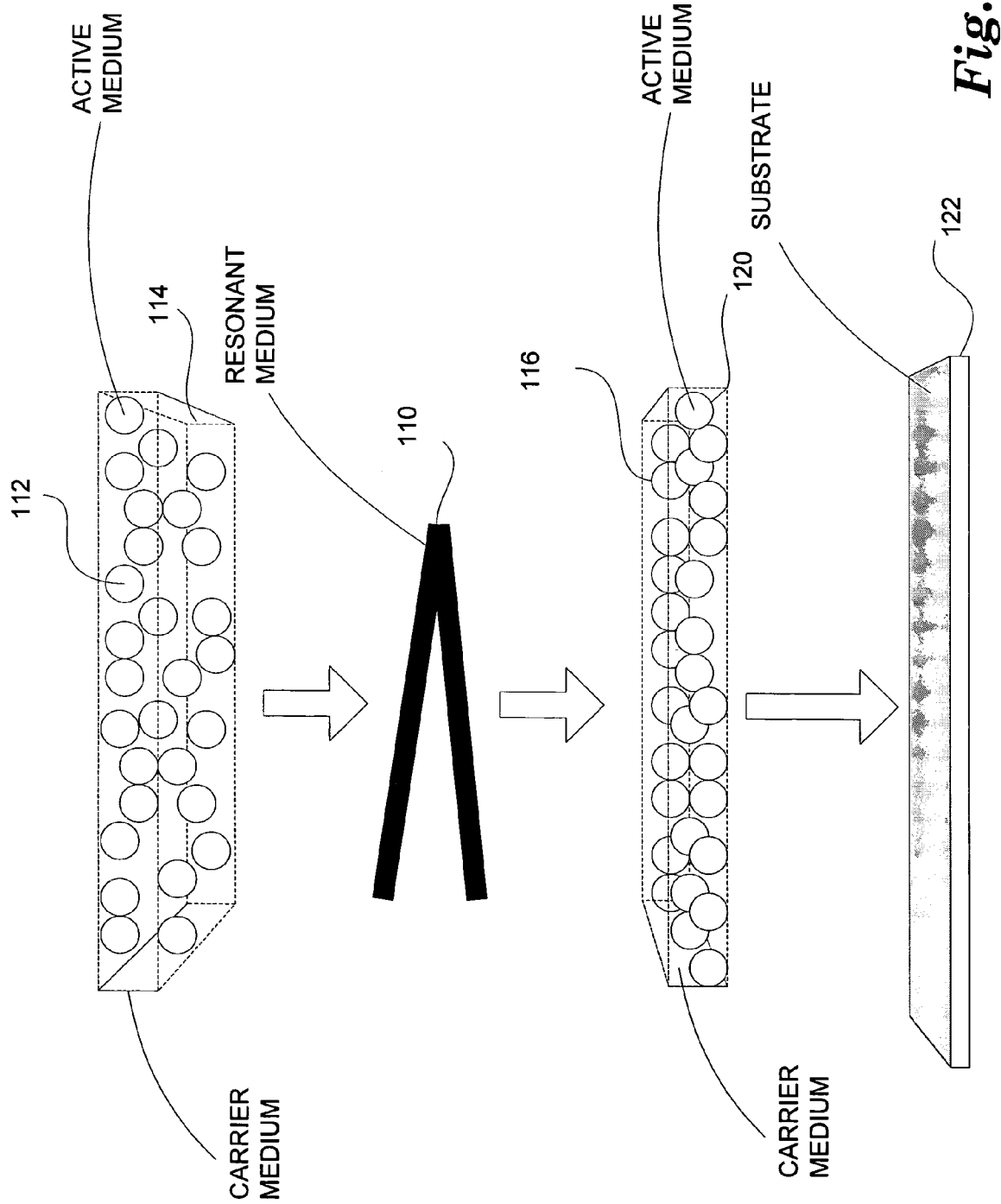
FIG. 1b is a block diagram illustrating the primary components of an alternative embodiment of the present invention.

In exemplary embodiments of the present invention, a nanostructure is used to generate a highly localized nanoscale optical field. The optical field is excited using Surface Plasmon Amplification by Stimulated Emission of Radiation (SPASER). The SPASER radiation consists of surface plasmons that undergo stimulated emission, but in contrast to photons can be localized within a nanoscale region. A SPASER can incorporate an active medium formed by two-level emitters, excited by an energy source, such as an optical, electrical, or chemical energy source. The active medium may be quantum dots, which transfer excitation energy by radiationless transitions to a resonant nanosystem that can play the same role as a laser cavity in a conventional laser. The transitions are stimulated by the surface plasmons in the nanostructure, causing the buildup of a macroscopic number of surface plasmons in a single mode.

The SPASER may not emit light waves, because its two-level emitters undergo radiationless transitions where their excitation energy is transformed into the quasi-static electric field energy of surface plasmons. There are a multitude of possible applications of the SPASER in nanoscience and nanotechnology, including for near-field non-linear optical probing and nanomodification.

A detailed summary of the theoretical aspects of the present invention are described in a paper authored by the inventors: D. J. Bergman and M. I. Stockman, *Surface Plasmon Amplification by Stimulated Emission of Radiation: Quantum Generation of Coherent Surface Plasmons in Nanosystems*, Phys. Rev. Lett. 90, 027402 (2003). That paper is hereby incorporated by reference. The contents of that paper were included in U.S. Provisional Application No. 60/437,760, filed on Jan. 3, 2003 and to which this patent application claims priority.

FIG. 1a is a block diagram illustrating the primary components to an exemplary embodiment of the present invention. In the embodiment of FIG. 1a, a SPASER device is depicted. Spaser is an acronym for surface plasmon amplification by stimulated emission of radiation. The SPASER device of FIG. 1a includes a resonant medium 100 that is located adjacent to an active medium 102. The active medium 102 is contained within a carrier medium 104. In the embodiment of FIG. 1a, the active medium 102 and the resonant medium are affixed adjacent to one another to a substrate 106.

In this embodiment of the present invention, the active medium 102 is placed adjacent and on top of the resonant medium 100. The resonant medium 100 is affixed to the substrate 106. The active medium 102 and/or the carrier medium 104 can be affixed to the resonant medium 100 or to the substrate 106. The active medium 102 may cover substantially the entire resonant medium 100, such that the resonant medium is substantially surrounded by the active medium 102; such a configuration is favorable for excitation of a broad range of surface-plasmon modes in the resonant medium. Alternatively, the active medium 102 may cover less than the entire resonant medium 100 for the purpose of mode selection: those surface-plasmon modes of the resonant medium with preferably be excited whose maxima are within the areas covered by the resonant medium.

The resonant medium may consist of a metal or composite (metal/semi-conductor/dielectric) nanoparticle that has surface plasmon modes in the ultraviolet, visible, or infrared region of the electromagnetic frequency spectrum. For example, the resonant medium 100 may be a silver nanosphere with a radius of between 10 and 50 nanometers (nm). Alternatively, the resonant medium may be a silver nanoshell with a thickness of between 5 and 20 nm and a radius of 50 nm. Those skilled in the art will appreciate that the resonant medium may be fabricated from various materials and of various sizes. Preferably, the resonant medium 100 will be fabricated of a metal or composite nanoparticle having low dielectric losses at the generation frequency. This characteristic has been observed by the inventors in nanoparticles of so-called coinage metals, including silver, platinum, and gold, in alkaline metals, and in aluminum.

The resonant medium 100 depicted in FIG. 1a is a nanoparticle in the form of a nanowedge. The nanowedge has a V-shaped form. The resonant medium nanoparticle 100 of FIG. 1a is approximately 30 nm in length (i.e., along its longitudinal axis from the vertex to the opening) and approximately 20 nm in width. Preferably, the resonant medium 100 is a material that supports (i.e., possesses) surface plasmons. Although FIG. 1a depicts the resonant medium 100 affixed to a substrate 106, those skilled in the art will appreciate that the resonant medium nanoparticle may be either free-standing or deposited on a substrate 106.

A second primary component of a SPASER device is the active medium 102. The active medium may contain objects having significant dipole oscillator strength for transitions at a desired frequency. Examples of such objects include rare-earth ions and semiconductor quantum dots. Those skilled in the art will appreciate that other known objects exhibit this characteristic. The transition frequency preferably overlaps with the spectral frequency range of surface plasmons (e.g., from ultraviolet frequencies to infrared frequencies). Free particles exhibiting such transitions also exhibit efficient fluorescence. The active medium 102 is a collection of fluorescent (i.e., chromophoric) particles. Preferably, the fluorescent particles of the active medium 102 are quantum dots. The active medium 102 depicted in the exemplary embodiment of FIG. 1a is embedded within a carrier medium 104. The combination of the active medium 102 and the carrier medium 104 comprises a nanosize layer that can be affixed to a substrate 106 and/or to the resonant medium 100. The shape of the active medium 102 can be designed to complement the size and structure of the resonant medium 100 such that the desired eigenmodes are generated.

The active medium 102 preferably comprises quantum dots. Quantum dots transfer their excitation energy by radiationless transition to a resonant nanostructure that fulfills the same role as a laser cavity in a conventional laser. The radiationless transitions are stimulated by the surface plasmons in the nanostructure, causing a buildup of a macroscopic number of surface plasmons in a single mode. Quantum dots are preferable, because of their desirable physical and chemical properties. Quantum dots are tunable in frequency due to quantum confinement. Quantum dots also have relatively large transitions dipoles and narrow transition lines and allow dense packing without compromising their optical properties. Quantum dots are well-known to be physically, chemically, and photochemically stable. Presently, there are two types of well-known quantum dots: nanocrystals grown chemically or quantum dots created by modification (including doping) of semiconductor surfaces. A surface class of nanocrystal quantum dots for the SPASER active medium is comprised of nanocrystals covered by a layer of organic molecules, which makes them even more chemically and mechanically stable.

The active medium 102 can be excited by an external energy source. Examples of external energy sources include optical energy sources, electrical energy sources and chemical energy sources. Although not likely to be feasible on the nanoscale, a nuclear energy source may also be used to excite the active medium 102. For optical excitation, the excitation frequency is different than the generated frequency of the SPASER nanostructure. When excited, the active medium 102 undergoes a resonant transition, whereby energy is transferred to surface plasmons in the resonant medium 100, as a result of electric interaction. The SPASER generates a localized radiation field due to the stimulated emission of surface plasmons.

As mentioned above, the stimulated emission of photons is a well-known phenomenon wherein the probability of a photon's emission in a certain state is proportional to the number of photons that are already present in that state. This is the phenomenon by which lasers sustain generation in a lasing mode. A similar theory applies to the stimulated emission of surface plasmons in a SPASER. Similar to a laser, a SPASER has the ability to concentrate energy in time. The SPASER stores energy during a comparatively long period and may emit the energy as an ultra short pulse. The pulse of a SPASER can be on the order of 100 fs. The SPASER generates optical fields defined to be nanoscale (sizes on the order of 1 to 100 nanometers). In near-field scanning optical microscopes, light is generated outside of the nanoscale range and channeled into the nanoscale range. The SPASER is significantly different in that it generates optical fields on the nanoscale and does not need channeling. Notably, the SPASER does not necessarily emit light. That is, a purely electric oscillating field is associated with plasmon emission and there is no significant magnetic field component in the localized field. In general, the SPASER is useful in applications where light is not needed, but there is a need for localized optical field generation. Applications for the SPASER are discussed in more detail in connection with FIGS. 6 and 7.

FIG. 1b is a block diagram illustrating the primary components of an alternative embodiment of the present invention. As stated above in connection with FIG. 1a, in certain cases it is preferable that the resonant medium 110 is surrounded by the active medium 112. However, in the embodiment in FIG. 1a, the active medium 102 is applied to the top of the resonant medium 100 and there is no active medium 102 under the resonant medium 100. That is, there is no active medium 102 between the resonant medium and the substrate 106. In the alternative embodiment of FIG. 1b, a second carrier medium 120 including suspended active medium 116 is affixed to a substrate 122 before the resonant medium 110 is affixed. The second carrier medium 114, including a second layer of active medium 112, is applied on top of the resonant medium 110. Accordingly, the resonant medium 110 is completely surrounded by or "sandwiched" in the active medium 112/116.

As stated above, those skilled in the art will appreciate that the substrates 106, 122 depicted in FIGS. 1a and 1b are optional and the SPASER device depicted in those figures can be implemented using a free-standing resonant medium. For the purposes of the description of the various embodiments of the present invention, the combination of the active medium and the carrier medium will be collectively referred to as the active medium. Those skilled in the art will appreciate that the carrier medium can be an inert, non-functional component of the SPASER, used only to provide desired structural characteristics to the active medium. Alternatively, the carrier medium may be completely absent if the aggregate of the emitters, e.g., quantum dots, is mechanically sufficiently stable. Yet another variation of the SPASER design may be that shown in FIG. 1b where the upper active-medium layer 114 is absent. In such a case, the layer 120 is deposited on the substrate 122, and the resonant medium 110 is affixed on top of it. Such a configuration can be advantageous for applications where the exposed resonant medium should be in the direct contact with or in close proximity to an external object. (e.g., a molecule or biological object for diagnostic purposes.)

Figure 2:
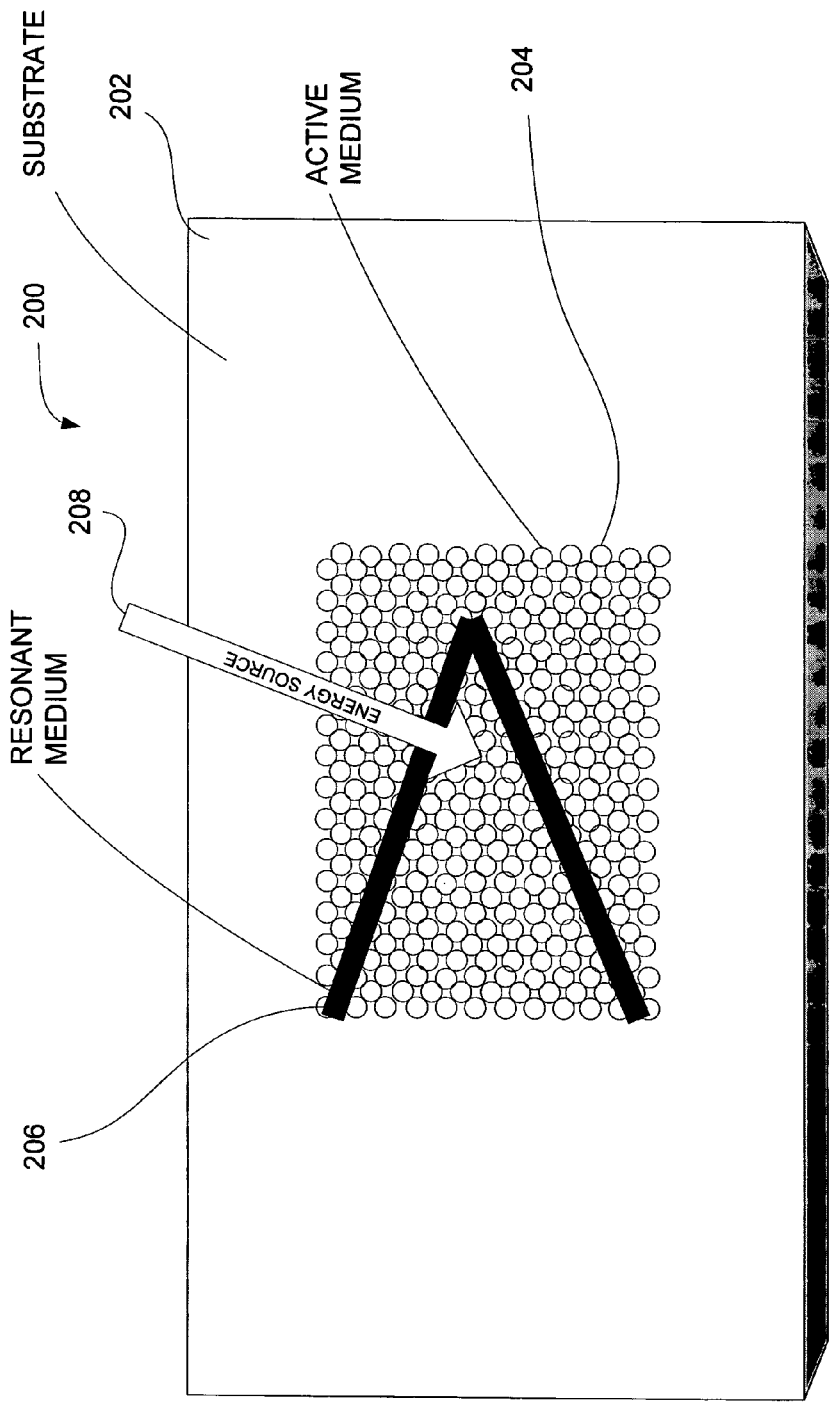
FIG. 2 is a block diagram depicting the application of energy to the active medium in an exemplary embodiment of the present invention.

FIG. 2 is a block diagram depicting the application of energy to the active medium in an exemplary embodiment of the present invention. The SPASER 200 of FIG. 2 comprises a resonant medium 206 and an active medium 204 deposited on a substrate 202. SPASER generation can be accomplished by applying energy to the active medium 204. An energy source 208 is used to apply energy to the active medium 204, thus exciting the active medium 204 and causing the emission of surface plasmons in the resonant medium 206. The energy source may be optical, electrical, chemical, or nuclear. The inventors contemplate that virtually any energy source that can excite the active medium can be used. In the case of an electrical energy source, nanoleads may be used to connect the active medium 204 to the electrical energy source. The nanoleads are not depicted in FIG. 2.

Figure 3:
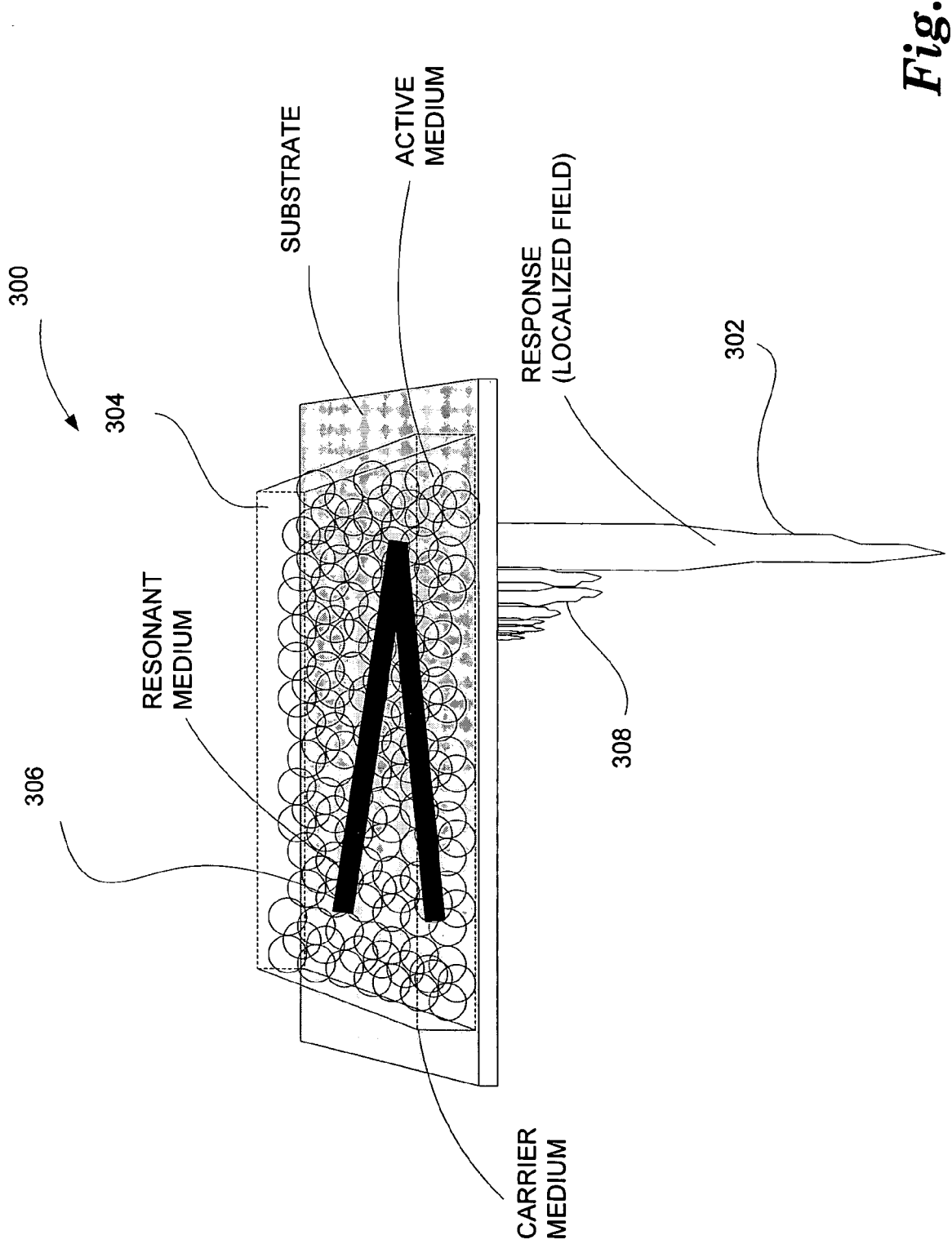
FIG. 3 is a block diagram depicting a highly localized, nanoscale, oscillating electric field that is generated in response to the application of energy to the active medium in an exemplary embodiment of the present invention.

FIG. 3 is a block diagram depicting a highly localized nanoscale electric field that is generated in response to the application of energy to an active medium 304 in an exemplary embodiment of the present invention. The SPASER device 300 of FIG. 3 generates a localized field response 302 when energy is applied to the active medium 304. The response 302 is generated at the apex of the nanowedge resonant medium 306 and is localized in that a high magnitude oscillating electric fields are located at or near the nanowedge vertex with significantly lower magnitude fields 308 in the near vicinity. Consequently, the SPASER device 300 can be used to apply a concentrated field to a target by placing the target in the vicinity of the localized field response 302. Advantageously, the magnitude of the localized field response 302 can be adjusted. The adjustability of the localized field response 302 is one characteristic of the SPASER device 300 that makes it useful for applications requiring fields of various energy levels. For example, a higher magnitude energy field may be used for writing data onto a storage medium than for reading data from the storage medium.

Figure 4:
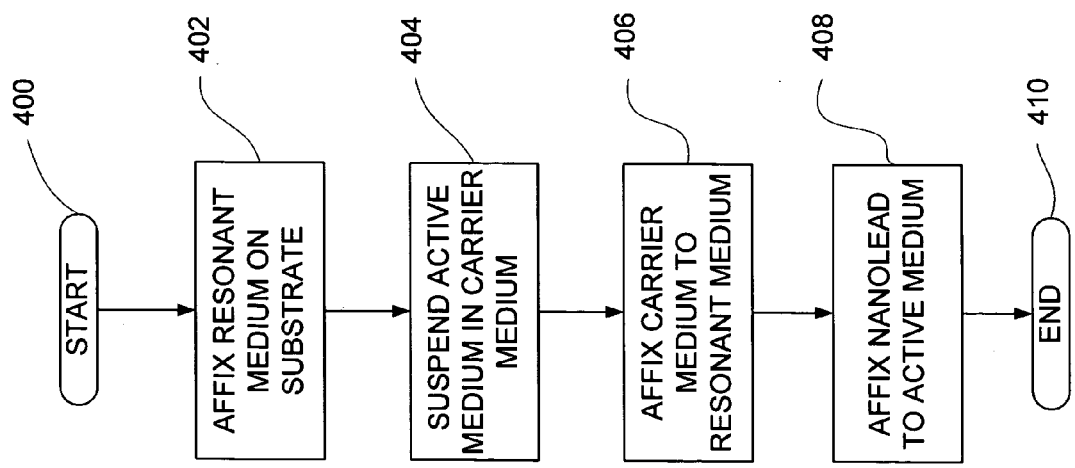
FIG. 4 is a flow chart depicting a method for building a SPASER device that is an exemplary embodiment of the present invention.

FIG. 4 is a flow chart depicting a method for building a SPASER device that is an exemplary embodiment of the present invention. The method of FIG. 4 begins at start block 400 and proceeds to step 402. At step 402, the resonant medium is affixed to a substrate. As described above in connection with FIGS. 1a through 3, the resonant medium may be affixed to a substrate or free standing. Accordingly, step 402 is optional.

The method proceeds from step 402 to step 404. At step 404, the active medium is suspended in a carrier medium. As described above, the carrier medium can be an inert material in that it provides only structural characteristics for supporting the active medium in a particular physical location. Alternatively, an active medium without a carrier medium, e.g., dry aggregate of quantum dots, also can be used. In such a case, step 404 is optional.

The method proceeds from step 404 to step 406. At step 406, the carrier medium is affixed to the resonant medium. As described in connection with FIG. 1b, the carrier medium (containing the active medium) can be affixed to the resonant medium, to the substrate, or to another carrier medium in the case where the resonant medium is surrounded by the carrier medium/active medium. The method of FIG. 4 proceeds from 406 to step 408.

At step 408, a nanolead is connected between an energy source and the active medium. As stated above, the nanolead is used for applications of the SPASER device wherein the active medium is excited using an electrical energy source. For applications wherein an energy source other than an electrical energy source is used, a nanolead may not be used and step 408 would then be optional. Those skilled in the art will appreciate that the nanolead may not be connected to an energy source upon the manufacture of the SPASER device, but may be connected only to the active medium such that the energy source may be connected upon use of the SPASER device. The method proceeds from step 408 to end block 410 and terminates.

Figure 5:
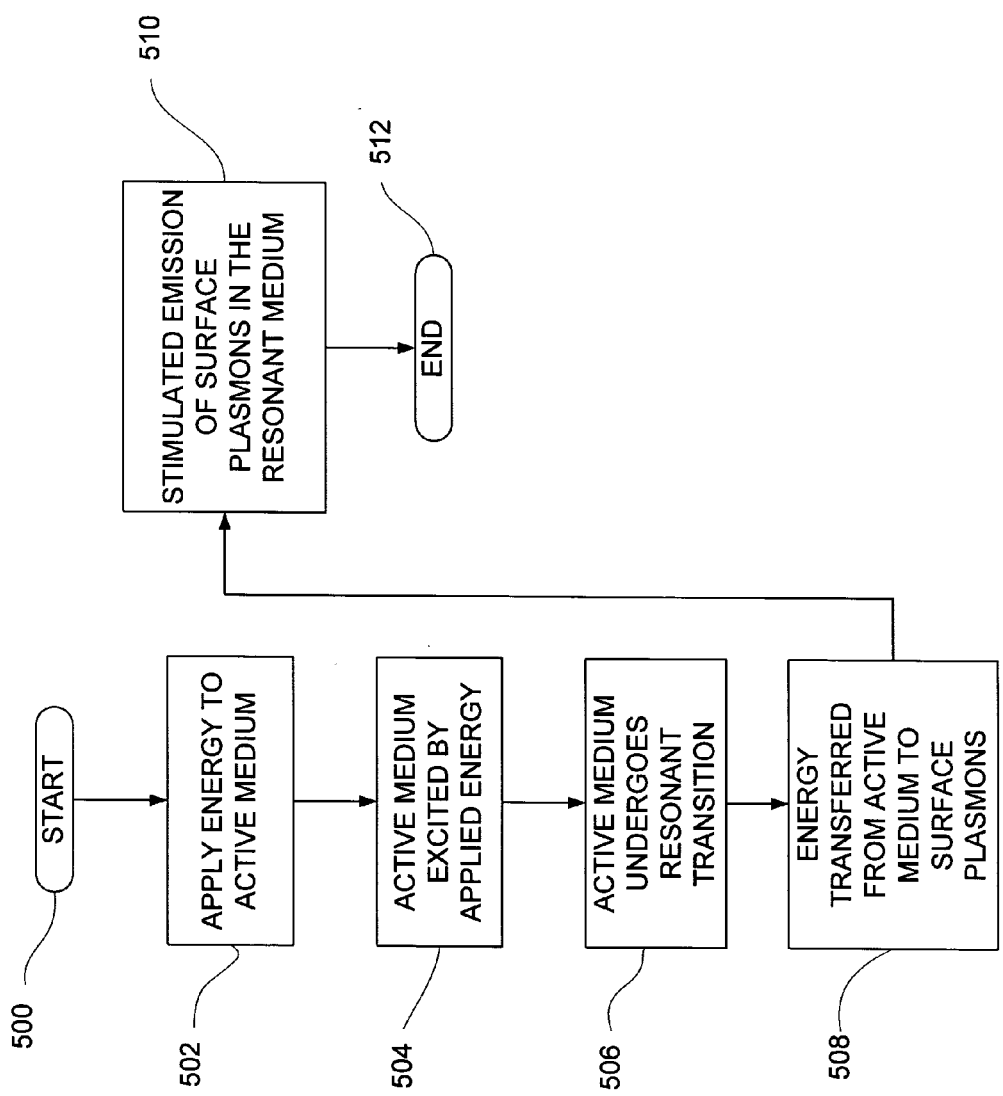
FIG. 5 is a flow chart depicting a method for generating a highly localized nanoscale electric field that is an exemplary embodiment of the present invention.

FIG. 5 is a flow chart depicting a method for generating a highly localized nanoscale electrical field that is an exemplary embodiment of the present invention. The method of FIG. 5 begins at start block 500 and proceeds to step 502. At step 502, energy is applied to the active medium. As described above, conventional energy sources include optical, electrical, chemical, and nuclear energy sources. The method proceeds from step 502 to step 504. At step 504, the active medium is excited by the applied energy. The method then proceeds to step 506, wherein the active medium undergoes resonant transition.

The method of FIG. 5 proceeds from step 506 to step 508. At step 508, energy is transferred from the active medium to the surface plasmons in the resonant medium. The method then proceeds to step 510, wherein the emission of surface plasmons in the resonant medium is stimulated. The method then proceeds to end block 512 and terminates.

Figure 6:
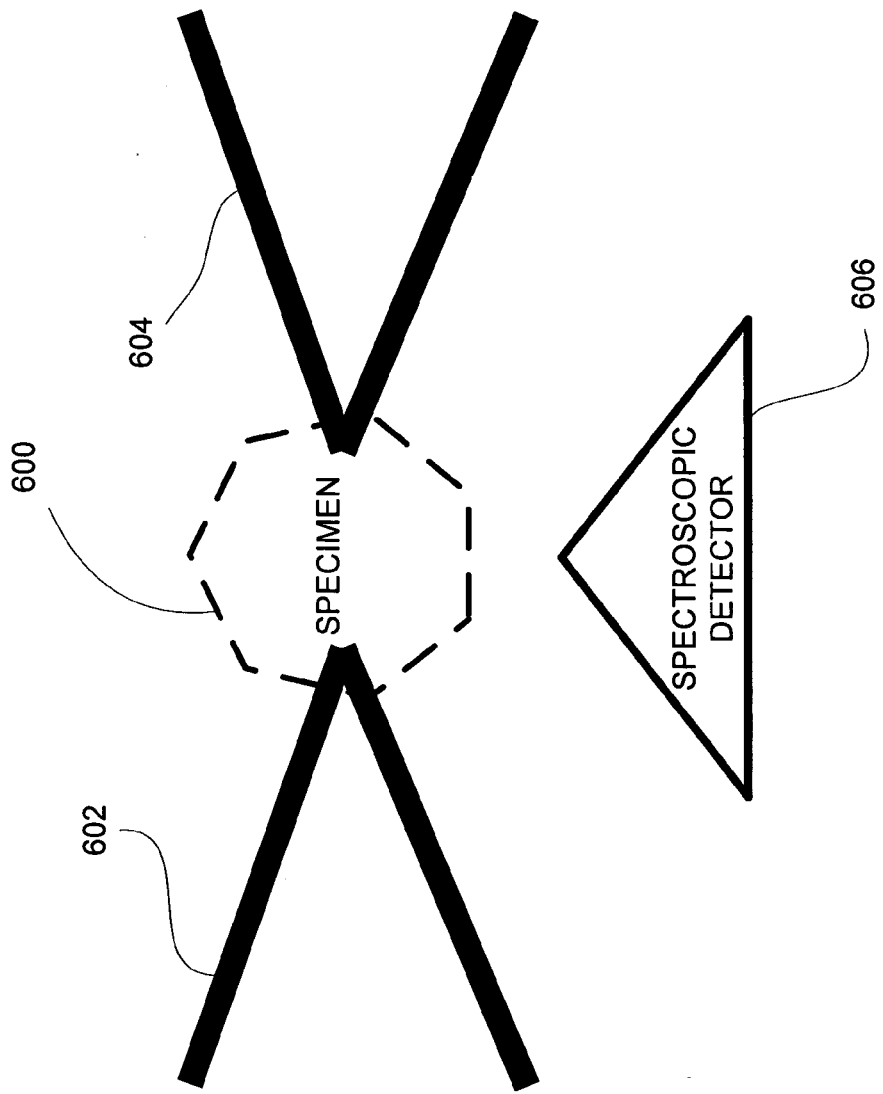
FIG. 6 is a block diagram depicting an exemplary spectroscopy application that is an exemplary embodiment of the present invention.

FIG. 6 is a block diagram depicting an exemplary spectroscopy application that is an exemplary embodiment of the present invention. In the spectroscopy application of FIG. 6, a nanosize specimen 600 is located near two SPASER devices 602, 604. The SPASER devices are energized as described above and produce SPASER responses that impact the specimen 600. The specimen may cause the Raman scattering of the SPASER fields. A spectroscopic detector 606 may be used to detect the scattering and to generate an output for the analysis of the scattering. For example, the spectroscopic detector 606 may be configured to identify certain characteristics of the specimen based on the scattering analysis. Because of the nanostructure of the SPASER device 602, 604, such specimen identification can be performed on a nanoscale. The applications for use of SPASER devices 602, 604 on the nanoscale are virtually limitless. For example, a single specimen comprising a single molecule, a single cell, or a single virus can be analyzed by one or more SPASER devices. Such a device might be used to detect the presence of a very small amount of a dangerous substance such as an anthrax spore, or a smallpox virus. While conventional devices exist for such detection, the use of a SPASER device in this application would enable significantly earlier detection of significantly smaller specimen sizes, down to a single molecule, virus, spore, or cell. High intensity local fields of a SPASER can be used to modify a molecule or a surface within a nanoscale region. This modification can be photochemical or photophysical (e.g., melting, evaporation, etc.).

Figure 7:
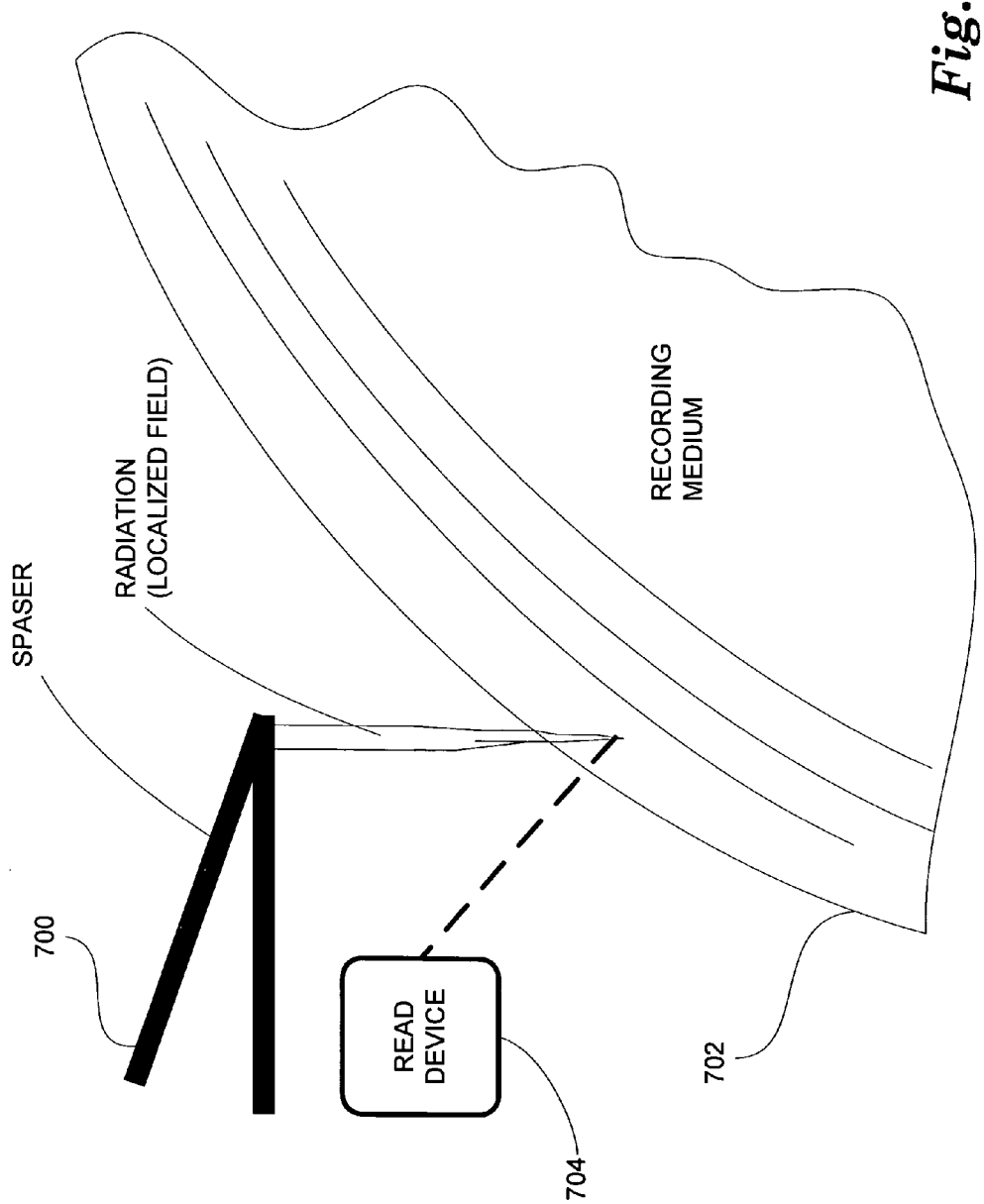
FIG. 7 is a block diagram depicting an exemplary electronic data storage and retrieval application that is an exemplary embodiment of the present invention.

FIG. 7 is a block diagram depicting an exemplary electronic data storage and retrieval application that is an exemplary embodiment of the present invention. As depicted in FIG. 7, a SPASER device 700 can be used to write (e.g., etch) bits of data on the surface of a recording medium 702. The SPASER device 700 may then be used in conjunction with a read device 704 to read data that has been previously recorded on the surface of the recording medium 702. The read device 704 may, for example, receive and analyze a radiation field that is emitted by the surface of the recording medium 702. The nanoscale operating range of the SPASER device 700 enables super-dense recording of data, such that the physical size requirements of the recording medium 702 can be significantly reduced. That is, significantly higher amounts of data can be stored on significantly smaller storage media, by using a SPASER device instead of conventional data writing devices.

Figure 8:
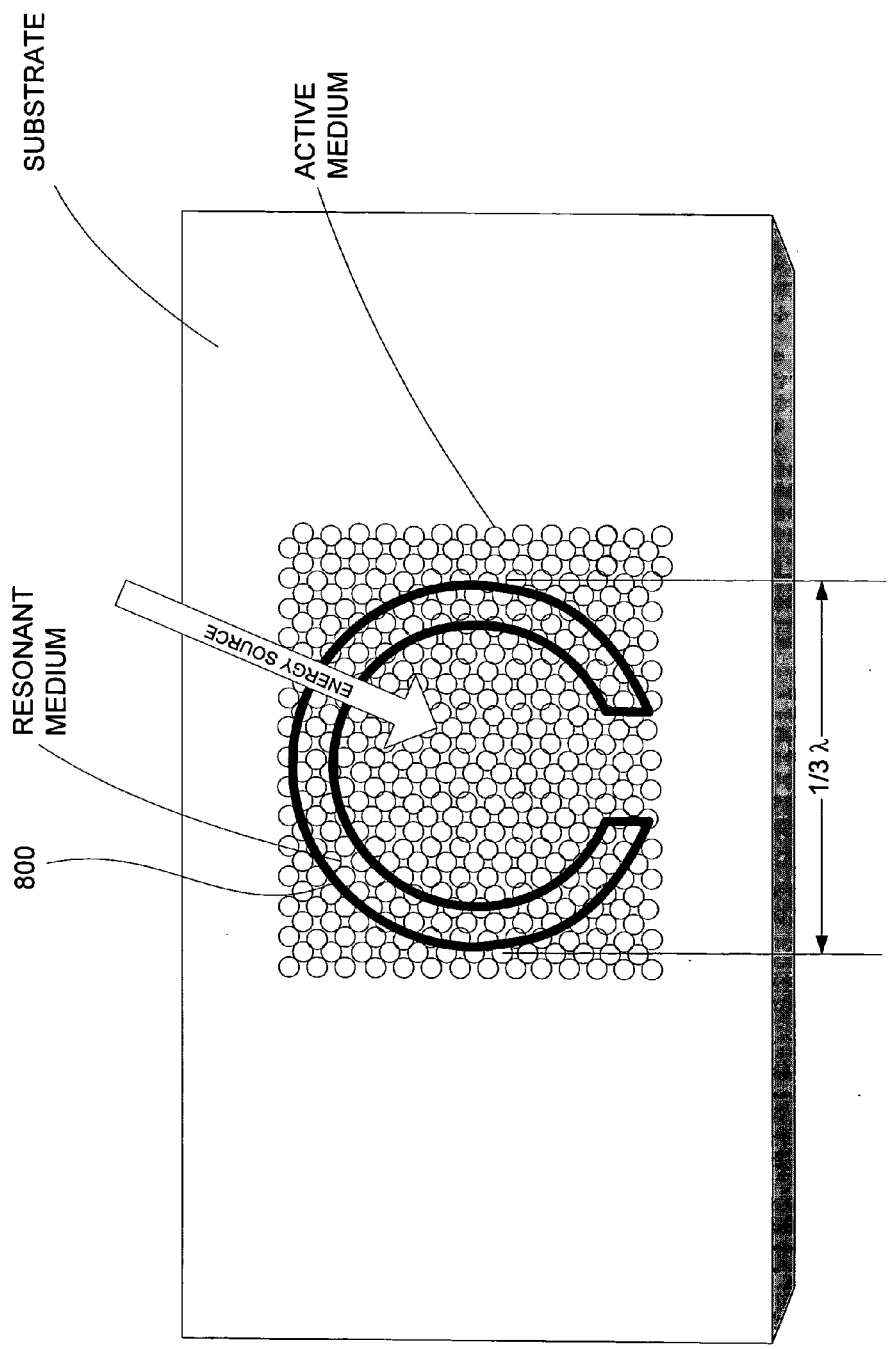
FIG. 8 is a block diagram of a pseudo-SPASER device that generates both localized electrical and magnetic fields that is an alternative embodiment of the present invention.

FIG. 8 is a block diagram of a pseudo-SPASER device that generates both localized electrical and magnetic fields. As described above, the SPASER device of various embodiments of the present invention is characterized by generation of an electric field with little or no magnetic component. The embodiment of FIG. 8 uses a resonant medium that has a split-ring configuration that generates both a localized electric field and a localized magnetic field. However, unlike the nanostructure of the SPASER device, the device of FIG. 8 has a much larger structure on the scale of a fraction of a wavelength of light. For example, the diameter of the split-ring resonant medium is one-third wavelength.

QUANTITATIVE DESCRIPTION OF AN EMBODIMENT OF THE INVENTION

An embodiment of the invention will now be described in quantitative terms. While not being limiting of the scope of the appended claims, the description will enable a skilled person to practice the claimed invention.

The explosive growth of nanoscience and nonotechnology during the past decade has also led to great interest and improved understanding of nanoscale optical fields, and to the development of tools for studying and exploiting them. In particular, such fields are excited at metallic nanoparticles or nanofeatures of metallic microparticles, where they are greatly enhanced due to high quality-factor surface Plasmon (SP) resonances. See, e.g., V. M. Shalaev and M. I. Stockman, ZhETF 92, 509 (1987) [Translation: Sov. Phys. JEPT 65, 287 (1987)]; A. V. Butenko, V. M. Shalaev, and M. I. Stockman, ZhETF 94, 107 (1988) [Translation: Sov. phys. JEPT, 67, 60 (1988)]; M. I. Stockman et al., Phys. Rev. B 46, 2821 (1992); M. I. Stockman et al., Phys. Rev. Lett. 72, 2486 (1994). These local fields are singular, exhibiting giant spatial fluctuations and energy concentration in nanosize volumes. See, e.g., M. I. Stockman et al., Phys. Rev. Lett. 72, 2486 (1994); M. I. Stockman, L. N. Pandey, and T. F. George, Phys. Rev. B 53, 2183 (1996); S. Gresillon et al., Phys. Rev. Lett. 82, 4520 (1999). Due to these "hot spots," the optical responses are gigantically enhanced and can be strong enough to allow, in particular, observation of Raman scattering from a single molecule attached to a metal colloidal particle. See, e.g., K. Kneipp et al., Phys. Rev. Lett. 78, 1667 (1997) and S. Nie and S. R. Emory, Science 275, 1102 (1997). A promising area is local optical nanosize probing by a metal tip that creates enhanced fields in its vicinity. This was demonstrated for near-field fluorescence microscopy based on two-photon excitation. See, e.g., E. J. Sanchez, L. Novotny, and X. S. Xie, Phys. Rev. Lett. 82, 4014 (1999). A theory of manipulation of particles by enhanced optical fields at a metal tip (optical nono-tweezers) was developed. See, e.g., L. Novotny, R. X. Bian, and X. S. Xie, Phys. Rev. Lett. 79, 645 (1997). It was suggested, quite early, to use local fields for linear and non-linear optical nanoprobing and nanomodification. See, e.g., M. I. Stockman, Autometria 3, 30 (1989) [Translation: Opto-electronics, Instrumentation and Data Processing 3, 27 (1989)].

The above phenomena and applications are based on the excitation of local fields in a nanostructure by a resonant external optical field. Significant limitations are imposed by this mode of excitation. In particular, only a very small fraction of the excitation field energy can be concentrated in the local field. It is almost impossible to select a single mode or a few modes to excite. Also, there exist a large number of dark eigenmodes that have desirable localization properties, but cannot be excited by an external wave. See, e.g., M. I. Stockman, S. V. Faleev, and D. J. Bergman, Phys. Rev. Lett. 87, 167401 (2001).

This embodiment of the invention illustrates a way to excite local fields using surface plasmon amplification by stimulated emission of radiation (spaser). The spaser radiation consists of SPs that are bosons and undergo stimulated emission, but in contrast to photons can be localized on the nanoscale. Spaser as a system will incorporate an active medium formed by two-level emitters, excited in the same way as a laser active medium: optically, or electrically, or chemically, etc. One promising type of such emitters are quantum dots (QDs). These emitters transfer their excitation energy by radiationless transitions to a resonant nanosystem that plays the same role as a laser cavity. These transitions are stimulated by the SPs already in the nanosystem, causing buildup of a macroscopic number of SPs in a single mode.

We consider a nanosystem formed by either metal or semi-conductor inclusions with dielectric function $\in(\omega)$, embedded in a dielectric host with dielectric constant $\in_h$. The classical field equation for the SP eigenmodes $\phi_n(r)$ and eigenvalues $s_n$ is:

$$\nabla \cdot [\theta(r) - s_n] \nabla \phi_n(r) = 0,$$

where $\theta(r)$ is the characteristic function, equal to 1 inside the inclusions and to 0 in the host. See, e.g., M. I. Stockman, S. V. Faleev, and D. J. Bergman, Phys. Rev. Lett. 87, 167401 (2001).

The actual SP frequencies $\Omega_n$ satisfy $s(\Omega_n) = s_n$, where $s(\omega) \equiv [1 - \in(\omega)\in_h]^{-1}$ is the spectral parameter. See, e.g., D. J. Bergman and D. Stroud, Solid State Physics, 46, 148, (1992). These frequencies are complex, $\Omega_n = \omega_n - i\gamma_n$, with real frequency $\omega_n$ and relaxation rate $\gamma_n$ of the n-th SP. For weak relaxation, $\gamma_n \ll \omega_n$, one finds that $\omega_n$ satisfies an equation $\text{Re}[s(\omega_n)] = s_n$ and that $$\gamma_n = \frac{\text{Im}[s(\omega_n)]}{s_n'}, \quad s_n' \equiv \frac{d\text{Re}[s(\omega)]}{d\omega}\bigg|_{\omega=\omega_n}. \quad (1)$$

Quantization of the SP system, valid in the quasi-static regime for times shorter than the SP lifetime $\tau_n \equiv 1/\gamma_n$, is carried out by using the following approximate expression for the energy H of an electric field E(r,t), which is obtained for a dispersive system by following L. D. Landau and E. M. Lifshitz, *Electrodynamics of Continuous Media* (Pergamon: Oxford and New York, 1984), Chap. 9, Section 80:

$$H = \frac{1}{4\pi T} \int_{-\infty}^{\infty} \frac{d[\omega\varepsilon(r,\omega)]}{d\omega} E(r,\omega) E(r,-\omega) \frac{d\omega}{2\pi} d^3 r. \quad (2)$$

Here T is an integration time used to calculate Fourier transforms, e.g., $\int_{-T/2}^{+T/2} E(r,\omega) e^{i\omega t} dt$. This time should satisfy $\tau_n \gg T \gg 1/\omega_n$, which is possible in the weak relaxation case, where the final results are independent of T. We expand the field operator $E(r,t) \equiv -\nabla \phi(r,t)$ in a series of the eigenstates $\phi_n(r)$:

$$\phi(r,t) = \sum_n \sqrt{\frac{2\pi\hbar s_n}{\varepsilon_h s_n'}} \varphi_n(r) e^{-\gamma_n t} [a_n e^{-i\omega_n t} + a_n^\dagger e^{i\omega_n t}], \quad (3)$$

where $a_n^\dagger$, $a_n$ are the creation and annihilation operators of a SP in the state $\phi_n(r)$. From Eq. (2), using Eq. (3), the quantized Hamiltonian takes on the standard harmonic oscillator form: $H = \sum_n \hbar\omega_n (a_n^\dagger a_n + 1/2)$.

Now assume an active host medium that we approximate as a collection of two-level dipolar emitters with population densities $\rho_0(r)$ and $\rho_1(r)$ in the ground and excited states, positioned at the points $r_a$, $a=1, 2, \ldots$ and having dipole moments $d^{(a)}$ with the transition matrix element $d_{10}$. The interaction of this active medium with the SP field is described by the perturbation $H' = \sum_a d^{(a)} \cdot \nabla \phi(r_a)$ to the system Hamiltonian.

Applying Fermi's golden rule to H', and taking into account Eqs. (1) and (3), we obtain a kinetic equation governing the number $N_n$ of SPs in the n-th mode:

$$\dot{N}_n = (A_n - \gamma_n) N_n + B_n. \quad (4)$$

Assuming an isotropic distribution of the transition dipoles, we calculate the Einstein coefficient $A_n$, which describes the net stimulated emission of SPs:

$$A_n = \frac{4\pi}{3\hbar} \frac{s'_n s_n |d_{10}|^2 p_n q_n}{\varepsilon_h [\text{Im} s(\omega_n)]^2} \gamma_n, \quad (5)$$

where $p_n$ is the spatial overlap factor of the population inversion and eigenmode intensity, $p_n = \int [\nabla \phi_n(r)]^2 [\rho_1(r) - \rho_0(r)] d^3 r$. The spectral overlap factor is $q_n = \int F(\omega)[1 + (\omega - \omega_n)^2 / \gamma_n^2]^{-1} d\omega$, where $F(\omega)$ is the normalized-to-1 spectrum of dipole transitions in the active medium, close to its fluorescence peak. The Einstein spontaneous emission coefficient $B_n$ is similar to $A_n$, but the excited state population $\rho_1$ replaces the population inversion $\rho_1 - \rho_0$ in the expression for $p_n$.

To discuss the behavior of this system, we introduce the dimensionless gain of the n-th eigenmode, $\alpha_n = (A_n - \gamma_n)/\gamma_n$. Quantum amplification and generation of SPs exist if $\alpha_n > 0$. For $\alpha_n$ approximately equal to 1 or greater, the spontaneous emission is unimportant. In this case, coherent generation occurs, and the number of SP's in a single eigenmode grows exponentially fast, $N_n$ being proportional to $\exp(\gamma_n \alpha_n t)$, eventually limited by the inversion depletion.

Consider some limiting cases. For the maximum population inversion, $\rho_1 \gg \rho_0$, and a thick active medium, a universal upper limit is approached, $P_n \approx \rho$, where $\rho = \rho_1 + \rho_0$ is the total density of the two-level energy donors. In this case, the gain does not depend on the field distribution of individual modes, but only on their frequencies. The factor $q_n$ depends on the width $\Gamma$ of the spectral function $F(\omega)$ as compared to the SP linewidth $\gamma_n$: For $\Gamma \gg \gamma_n$, $q_n \approx \gamma_n/\Gamma$, while in the opposite case $\Gamma \ll \gamma_n$, assuming that the donor transition is centered at the SP frequency, we have $q_n \approx 1$.

Figure 9A:
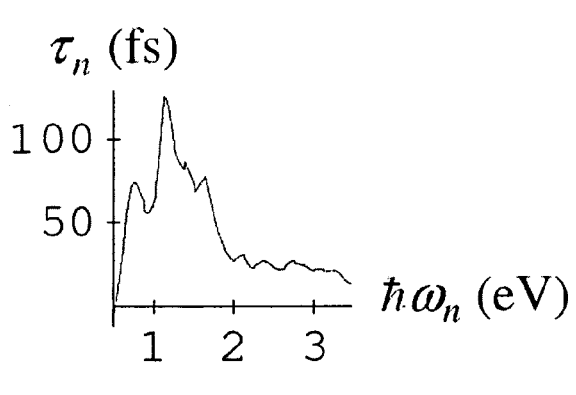
FIG. 9a is a chart showing calculated SP lifetimes for a range of energy values.

The SP lifetime $\tau_n$ (mostly due to dephasing) should be long enough to enable the spaser to generate or amplify local fields; it also defines the temporal scale of the evolution of these fields [cf. Eqs. (4) and (5)]. Our numerical results reported below are for inclusions made of metallic silver. Silver has the smallest value of $\text{Im}(\varepsilon)$ for any natural metal in the visible and near infrared (NIR) optical regions. See, e.g., P. B. Johnson and R. W. Christy, Phys. Rev. B 6, 4370 (1972). Such systems therefore exhibit the largest values of $\tau_n$. FIG. 9a shows calculated SP lifetimes $\tau_n$ that are comparatively long (50-120 fs) for 1.7 eV $> \hbar\omega_n > 0.8$ eV. This also implies that the spaser will be relatively fast, capable of generating pulses as short as approximately 100 fs or less.

Figure 9B:
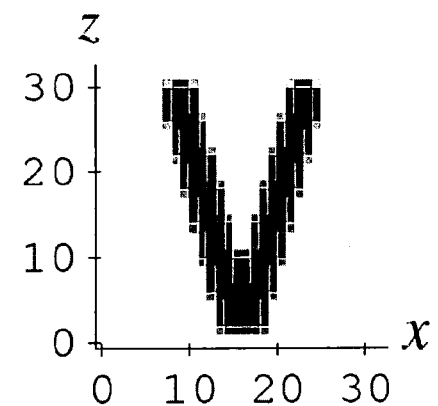
FIG. 9b is a chart showing a flat v-shaped metallic nano-inclusion positioned in the central xz-plane of a dielectric host.

The specific geometry of a metal/dielectric nanosystem that we consider was introduced in a previous publication on ultrafast responses by the inventors of this patent application. See M. I. Stockman, S. V. Faleev, and D. J. Bergman, Phys. Rev. Lett. 88, 067402 (2002). This is a flat V-shaped metallic nano-inclusion positioned in the central xz-plane of the dielectric host, as illustrated in FIG. 9b. This V-shape is two grid steps (2 to 10 nm) thick in the y direction. We assume that the active host medium has a planar distribution of emitters parallel to this V-shaped inclusion and consider two cases: In a thin medium, the two-level emitters occupy the central grid plane (except for the volume occupied by the V-shape itself), as well as the two neighboring grid planes above and below that plane, resulting in a total thickness of three grid steps (from 3 to 15 nm). In the opposite case of a thick medium, the emitters occupy all the host volume. In all cases we assume $\rho_1 = \rho$ and $q_n = 1$, as already discussed.

Emission in the NIR, where spasing is expected, imposes stringent requirements on the two-level emitters. Infra-red dyes are inefficient and not very stable at room temperature. Two other possibilities are rare-earth ions and semiconductor quantum dots (QDs). The latter seem the most promising, since they are tunable in frequency due to quantum confinement, have relatively large transition dipoles $d_{10}$ and narrow transition lines, and allow dense packing without compromising their optical properties. See, e.g., V. I. Klimov et al., Science 290, 314 (2000). The well-studied CdSe QDs emit at visible frequencies, too high for the spaser medium in this embodiment of the invention. The novel PbS and PbSe QDs can be synthesized with radii $R_D = 1-8$ nm to have transition energies 0.71—1.8 eV, which are ideally suited for spasing. See, e.g., A. Lipovskii et al., Appl. Phys. Lett. 71, 3406, (1997); K. Wundke et al., Appl. Phys. Lett., 76, 10 (2000).

The dipole element for the $1S_e \leftrightarrows 1S_h$ transition in QDs can be estimated from Kane's theory, conventionally assuming strong overlap of the envelope states, as:

$$d_{10} = e \sqrt{fK/(2m_0 \omega_n^2)},$$

where f is the transition oscillator strength, $K \approx 3$eV is Kane's interband parameter, and $m_0$ is the bare electron mass. Setting $f \approx 1$, which somewhat underestimates $d_{10}$ as well as the consequent gain, we obtain $d_{10} = 1.9 \cdot 10^{-17}$ esu.

We estimate $\varepsilon_h$ from the Maxwell Garnett formula assuming a dense packing of QDs in vacuum and adopting the known value of approximately 23 for the dielectric constant of PbS and PbSe, obtaining $\varepsilon_h = 6.6$. The QD spectral width $\Gamma$ is mostly due to the inhomogeneous broadening. In chemically synthesized QDs, $\Gamma$ is small enough, $\Gamma$ is of the same order of $\gamma_n$, yielding a value for $q_n$ approximately equal or less than 1, which is sufficient for spasing. See, e.g., V. I. Klimov et al., Science 290, 314 (2000).

Because both $d_{10}$ and $\varepsilon_h$ are essentially independent of the QD size, Einstein's stimulated emission coefficient $A_n$ in Eq. (5) and, consequently, the spaser gain $\alpha_n$, are higher for smaller QDs, with $A_n$ being proportional to $\rho$, which in turn is proportional to $R_D^{-3}$. For our computations, we chose a moderately small $R_D = 2.3$ nm, to be on the conservative side in estimating the gain.

Figure 10A:
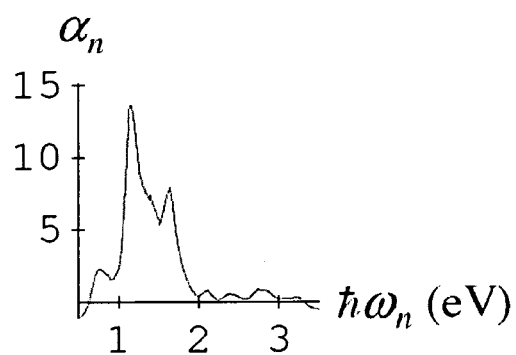
FIGS. 10a and 10b are charts showing SPASER gain as a range of energy values.
Figure 10B:
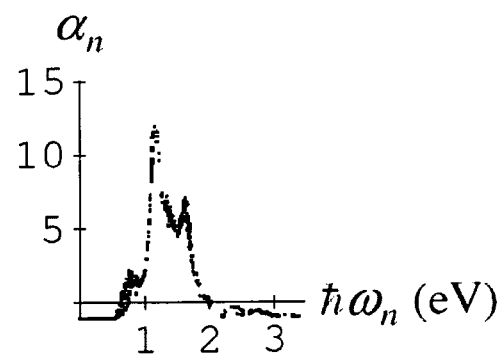

The spaser gain $\alpha_n$ is displayed in FIG. 10a and 10b vs. $\hbar\omega_n$ for both a thick and a thin medium. High values of $\alpha_n$, up to 12, are predicted for the latter (FIG. 10b). The maximum value of $\alpha_n$ is even greater for the thick medium, and the amplification spectral band is wider (FIG. 10a). The similarity in response of these two samples is due to the strong localization near the metal surface of the efficient spasing modes: only those QDs contribute that are positioned in the areas filled by these modes. The large gain for a thin (a few monolayers) QD active medium which surrounds the metal inclusion is advantageous: a spaser is possible whose total size is on the nanoscale.

Figure 11A:
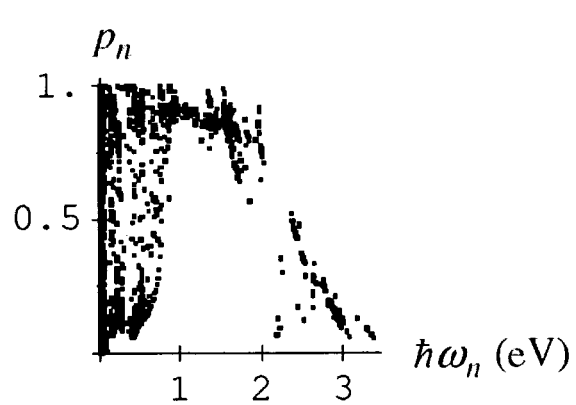
FIG. 11a is a chart showing fluctuations of the overlap feature from mode to mode.

In a thin active medium (FIG. 10b), the function $\alpha_n(\hbar\omega_n)$ exhibits some irregularities ("noise"). These come from fluctuations of the overlap factor $p_n$ from mode to mode, illustrated in FIG. 11a, which reflect the chaotic nature of these modes. Fortunately, the gain is maximal for $\hbar\omega_n$ between 1.1 eV and 1.9 eV, where these fluctuations are small. When gold replaces silver, computations indicate (data not shown) a positive gain $\alpha_n$ only if $R_D < 2$ nm, and $\alpha_n$ values that are significantly smaller. This is due to the higher losses in gold.

As we showed previously, there exist dark eigenmodes which cannot be excited or observed from the far field (wave) zone. See, e.g., M. L. Stockman, S. V. Faleev, and D. J. Bergman, Phys. Rev. Lett. 87, 167401 (2001). Among them are all the Anderson-localized eigenmodes. An important question is whether these dark eigenmodes can be excited (generated) in spaser. This is not only a principal fundamental question, but is also of significant importance for applications: Strongly localized dark eigenmodes excited in a spaser are promising for nanometer probing and high-field nanoscale photomodification.

Figure 11B:
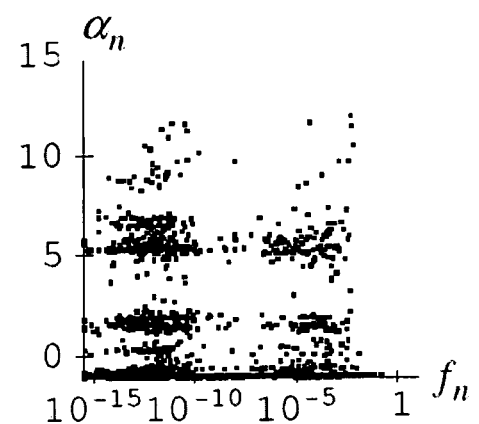
FIG. 11b is a chart showing gain factor as a function of oscillation strength for every eigenmode.

The ability of the spaser to excite both luminous and dark eigenmodes, including the strongly localized ones, is clearly demonstrated by the data of FIG. 11b, where we plot the gain factor $\alpha_n$ vs. the oscillator strength $f_n$ for every eigenmode. The eigenmodes with $f_n < 10^{-7}$ can be considered as dark, and those with $f_n$ equal to approximately $10_{-7}$ or greater as luminous. From FIG. 11, we conclude that the highest-gain eigenmodes ($\alpha_n$ equal to approximately 10 or greater) are quite rare and almost equally divided between dark and luminous.

When the spaser amplification condition $\alpha_n > 0$ is satisfied, a generating n-th eigenmode accumulates a macroscopic number $N_n$ of coherent SPs, which induces a local field of root-mean-square (RMS) magnitude $$E(r) = \langle [\nabla \phi(r)]^2 \rangle^{1/2} = E_n(r)(N_n + 1/2)^{1/2}; \quad (6)$$

$$E_n(r) = [4\pi \hbar s_n (\nabla \varphi_n(r))^2 / \varepsilon_h s'_n]^{1/2}.$$

In FIGS. 12a through 12d, we show the RMS amplitude $E_n(r)$ in the metal nanostructure plane for eigenmodes with the highest spaser gains at the two spectral maxima $\hbar\omega_n \approx 1.16$ eV (FIG. 12a and 12b), and $\hbar\omega_n \approx 1.6$ eV (FIG. 12c and 12d). The highest gain occurs for a luminous eigenmode (FIG. 12a) with $\hbar\omega_n = 1.15$ eV (cf. FIGS. 9 and 10). This eigenmode is concentrated within a radius a ≈15 nm around the tip of the V-shape. The spasing of this mode will be seen in the far zone as almost isotropic radiation with an anomalously narrow spectrum (high temporal coherence) and high spectral intensity. A dense enough ensemble of spasers may actually form a laser developing also spatial coherence.

Another high gain spaser eigenmode at $\hbar\omega_n = 1.18$ eV, displayed in FIG. 12b, is a completely dark eigenmode that creates very high local fields of approximately $7 \cdot 10^7 (N_n + 1/2)^{1/2}$ V/m, which are only a few orders of magnitude below atomic-strength fields. These fields are sharply localized at the tip of the nanostructure providing a unique tool for possible applications in nanoscale optical probing and modification where the undesirable, background far-zone radiation from t.he tip itself is absent.

In the second spectral maximum, the spaser eigenmodes at $\hbar\omega_n = 1.63$ eV (FIG. 12c) and 1.56 eV (FIG. 12d) are similar in some but not all respects to those in FIGS. 12a and 12b discussed above: A dark eigenmode at 1.63 eV is now delocalized, while a luminous eigenmode at 1.56 eV is strongly localized at the tip. However, the gains of these eigenmodes are about half of those at approximately 1.16 eV. Note that the selection of this vs. the previous group of eigenmodes can be done by tuning the transition frequency of QDs by selecting their sizes. At a given frequency, an eigenmode can be selected by positioning QDs in the region where its local fields are maximal.

The present quantum-plasmonics theory may have applications other than spaser. One such application is based on the fact that the Hamiltonian is a functional of the system geometry on the nanoscale, namely $H = \Sigma_n \hbar\omega_n [\theta(r)](N_n + \frac{1}{2})$. This brings about mechanical stresses in the system which depend on the level of excitation, but exist even for $N_n = 0$ (Casimir effect).

To summarize, this embodiment of the invention illustrates the spaser effect and prospective quantum-nanoplasmonic device. Spaser is not a laser: Its two-level emitters (QDs, in particular) do not emit light waves, but rather undergo radiationless transitions where their excitation energy is transformed into quasi-static electric field energy of SPs. The stimulated nature of this energy transfer causes buildup of macroscopic numbers of coherent SPs in individual eigenmodes of a nanosystem. It is possible to generate dark SPs that do not couple to far-zone fields. Spaser generates intense, nanoscale-localized optical-frequency fields with many possibilities for prospective applications in nanoscience and nanotechnology, in particular for near-field nonlinear-optical probing and nanomodification.

Although the present invention has been described in connection with various exemplary embodiments, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed is:

1. An apparatus for generating a nanoscale oscillating electric field via surface plasmon amplification by stimulated emission of radiation (SPASER), comprising:
   a resonant medium having at least one surface plasmon mode therein;
   an active medium, having a transition frequency and comprising at least one object having a significant transition strength; and
   an energy source;
   wherein the application of energy from the energy source to the active medium results in the energy transition of the at least one object, thereby causing population inversion in the active medium and stimulating the emission of the at least one surface plasmon in the resonant medium, and
   wherein the energy source provides a power exceeding a threshold so as to satisfy the SPASER action condition αn >0, where αn=(An−γn)/γn is a dimensionless gain, γn is the relaxation rate of the at least one surface plasmon mode, and A is Einstein's coefficient describing the net stimulated emission rate of the at least one surface plasmon mode, An being proportional to said transition strength and to a spatial overlap factor between said population inversion and the intensity of said at least one surface plasmon mode,
   whereby said SPASER action causes the buildup of a macroscopic number of surface plasmons in the at least one surface plasmon mode.

2. The apparatus of claim 1, wherein the resonant medium is affixed to a substrate.

3. The apparatus of claim 1, wherein the resonant medium is a nanowedge.

4. The apparatus of claim 1, wherein the resonant medium is a metal nanoparticle.

5. The apparatus of claim 1, wherein the resonant medium is a composite nanoparticle.

6. The apparatus of claim 5, wherein the composite nanoparticle comprises a metal.

7. The apparatus of claim 5, wherein the composite nanoparticle comprises a semiconductor.

8. The apparatus of claim 5, wherein the composite nanoparticle comprises a dielectric.

9. The apparatus of claim 1, wherein the resonant medium has surface plasmon modes in the visible region of the electromagnetic frequency spectrum.

10. The apparatus of claim 1, wherein the resonant medium has a plurality of surface plasmon modes in an ultraviolet region of the electromagnetic frequency spectrum.

11. The apparatus of claim 1, wherein the resonant medium has surface plasmon modes in the infrared region of the electromagnetic frequency spectrum.

12. The apparatus of claim 1, wherein the resonant medium is approximately 30 nanometers long.

13. The apparatus of claim 1, wherein the resonant medium is approximately 20 nanometers wide.

14. The apparatus of claim 1, wherein the object of the active medium is a rare-earth ion.

15. The apparatus of claim 1, wherein the object of the active medium is a dye molecule.

16. The apparatus of claim 1, wherein the object of the active medium is a semiconductor quantum dot.

17. The apparatus of claim 16, wherein the quantum dot is a doped semiconductor.

18. The apparatus of claim 16, wherein the quantum dot is a nanocrystal covered with a layer of organic molecules.

19. The apparatus of claim 16, wherein the semiconductor quantum dot is one of a PbS quantum dot and a PbSe quantum dot.

20. The apparatus of claim 16, wherein the semiconductor quantum dot is a chemically synthesized quantum dot.

21. The apparatus of claim 16, wherein the semiconductor quantum dot has a radius smaller than approximately 2.3 nm.

22. The apparatus of claim 21, wherein the semiconductor quantum dot has a radius smaller than approximately 2.0 nm.

23. The apparatus of claim 1, wherein the transition frequency of the active medium is substantially within the electromagnetic frequency range of visible light.

24. The apparatus of claim 1, wherein the transition frequency of the active medium is substantially within the electromagnetic frequency range of ultraviolet light.

25. The apparatus of claim 1, wherein the transition frequency of the active medium is substantially within the electromagnetic frequency range of infrared light.

26. The apparatus of claim 1, wherein the energy source is an optical energy source.

27. The apparatus of claim 1, wherein the energy source is an electrical energy source.

28. The apparatus of claim 24, wherein the electrical energy source is coupled to the active medium by nanoleads or a nanolead.

29. The apparatus of claim 1, wherein the energy source is a chemical energy source.

30. The apparatus of claim 1, wherein the energy source is a nuclear energy source.

31. The apparatus of claim 1, wherein the resonant medium comprises silver.

32. The apparatus of claim 1, wherein the resonant medium is a V-shaped metallic nano-inclusion.

33. The apparatus of claim 1, wherein the active medium is a few monolayers thick.

* * * * *